US010420868B2

(12) United States Patent
Long et al.

(10) Patent No.: US 10,420,868 B2
(45) Date of Patent: *Sep. 24, 2019

(54) SYSTEM AND METHOD FOR INTERFACING WITH A REDUCED PRESSURE DRESSING

(71) Applicant: KCI Licensing, Inc., San Antonio, TX (US)

(72) Inventors: Justin Alexander Long, San Antonio, TX (US); Aidan Marcus Tout, Alderbury (GB); Larry Tab Randolph, San Antonio, TX (US); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 894 days.

This patent is subject to a terminal disclaimer.

(21) Appl. No.: 14/185,326

(22) Filed: Feb. 20, 2014

(65) Prior Publication Data
US 2014/0180226 A1    Jun. 26, 2014

Related U.S. Application Data

(63) Continuation of application No. 13/183,929, filed on Jul. 15, 2011, now Pat. No. 8,690,845.
(Continued)

(51) Int. Cl.
A61M 5/00 (2006.01)
A61M 1/00 (2006.01)
(Continued)

(52) U.S. Cl.
CPC ........ *A61M 1/0088* (2013.01); *A61M 1/0094* (2014.02); *A61M 2205/3344* (2013.01)

(58) Field of Classification Search
CPC .......... A61M 5/00; A61M 5/32; A61M 25/00; A61M 35/00; A61M 1/00; A61M 5/178; A61F 13/00; A61F 7/00
See application file for complete search history.

(56) References Cited

U.S. PATENT DOCUMENTS 1,355,846 A   10/1920 Rannells
2,547,758 A    4/1951 Keeling
(Continued)

FOREIGN PATENT DOCUMENTS

AU    550575 A1   3/1986
AU    745271      4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
(Continued)

*Primary Examiner* — Tatyana Zalukaeva
*Assistant Examiner* — Ilya Y Treyger

(57) ABSTRACT

Systems, devices, and methods for treating a tissue site on a patient with reduced pressure are presented. In one instance, a reduced-pressure interface includes a conduit housing having a cavity divided by a dividing wall into a reduced-pressure-application region and a pressure-detection region. The reduced-pressure interface further includes a reduced-pressure port disposed within the reduced-pressure-application region, a pressure-detection port disposed within the pressure-detection region, and a base connected to the conduit housing, the base having a manifold-contacting surface. The dividing wall includes a surface substantially coplanar with the manifold-contacting surface.

25 Claims, 7 Drawing Sheets

Related U.S. Application Data

(60) Provisional application No. 61/365,252, filed on Jul. 16, 2010.

(51) Int. Cl.
    *A61M 5/32*      (2006.01)
    *A61M 25/00*     (2006.01)
    *A61M 35/00*     (2006.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0079852 A1 | 4/2006 | Bubb et al. |
| 2007/0219512 A1 | 9/2007 | Heaton et al. |

FOREIGN PATENT DOCUMENTS

| | | |
|---|---|---|
| AU | 755496 | 2/2002 |
| CA | 2005436 | 6/1990 |
| CN | 101378796 A | 3/2009 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |
| WO | 2009070905 A1 | 6/2009 |
| WO | 2009071935 A1 | 6/2009 |

OTHER PUBLICATIONS

Louis C. Argenta, MD and Michael J. Morykwas, PhD; "Vacuum-Assisted Closure: A New Method for Wound Control and Treat-

(56) References Cited

OTHER PUBLICATIONS ment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hyperemia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).

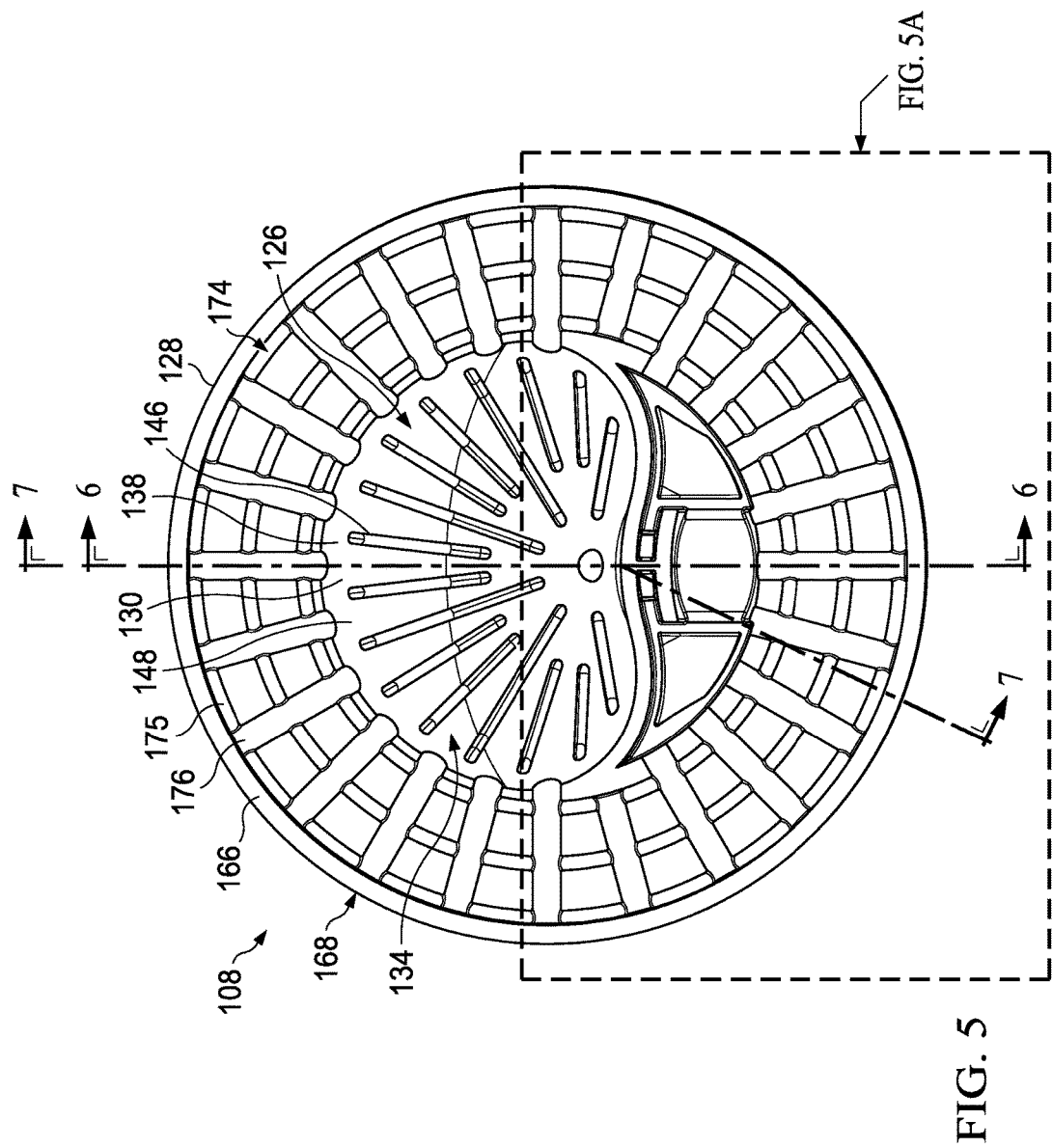

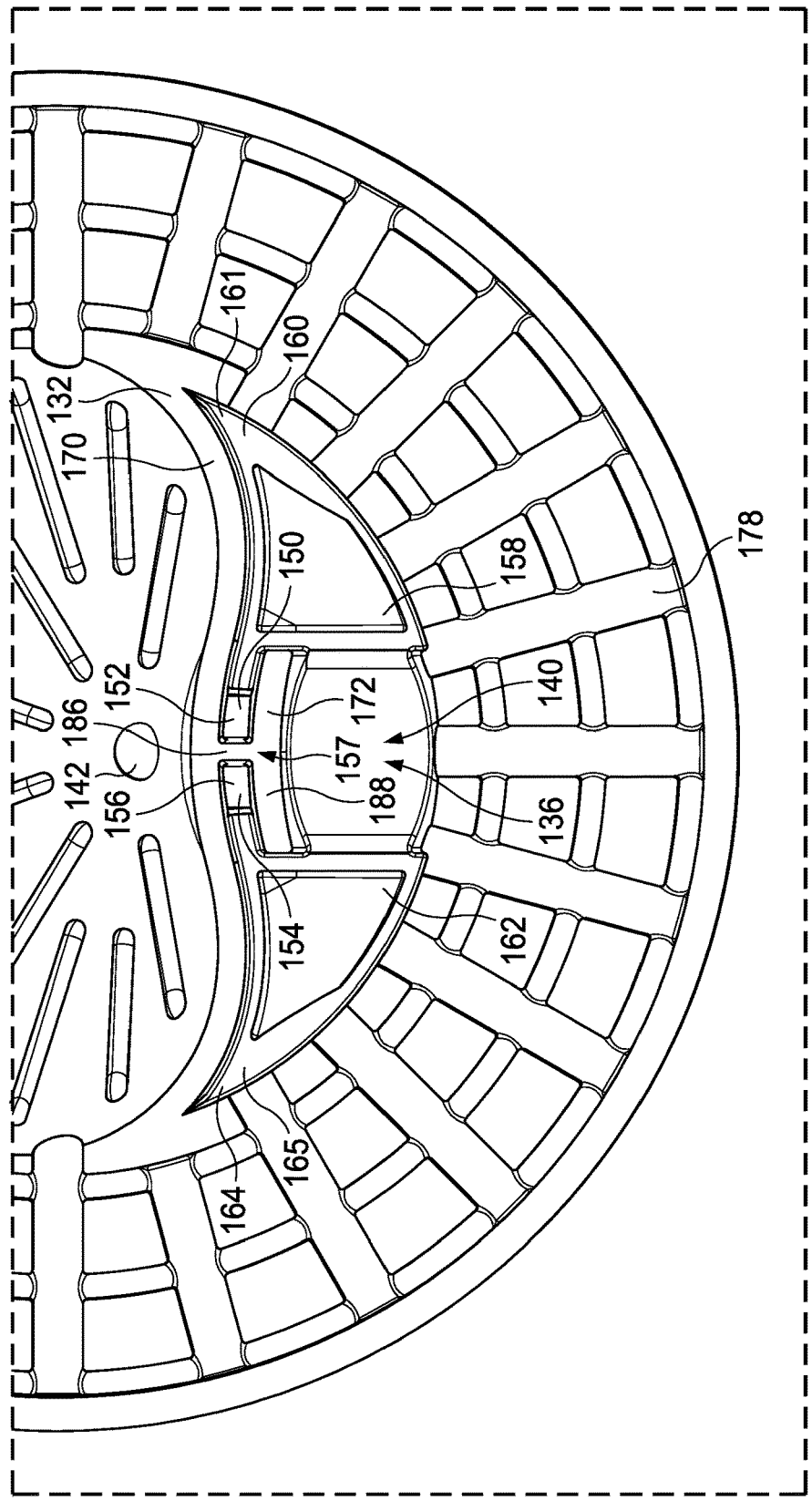

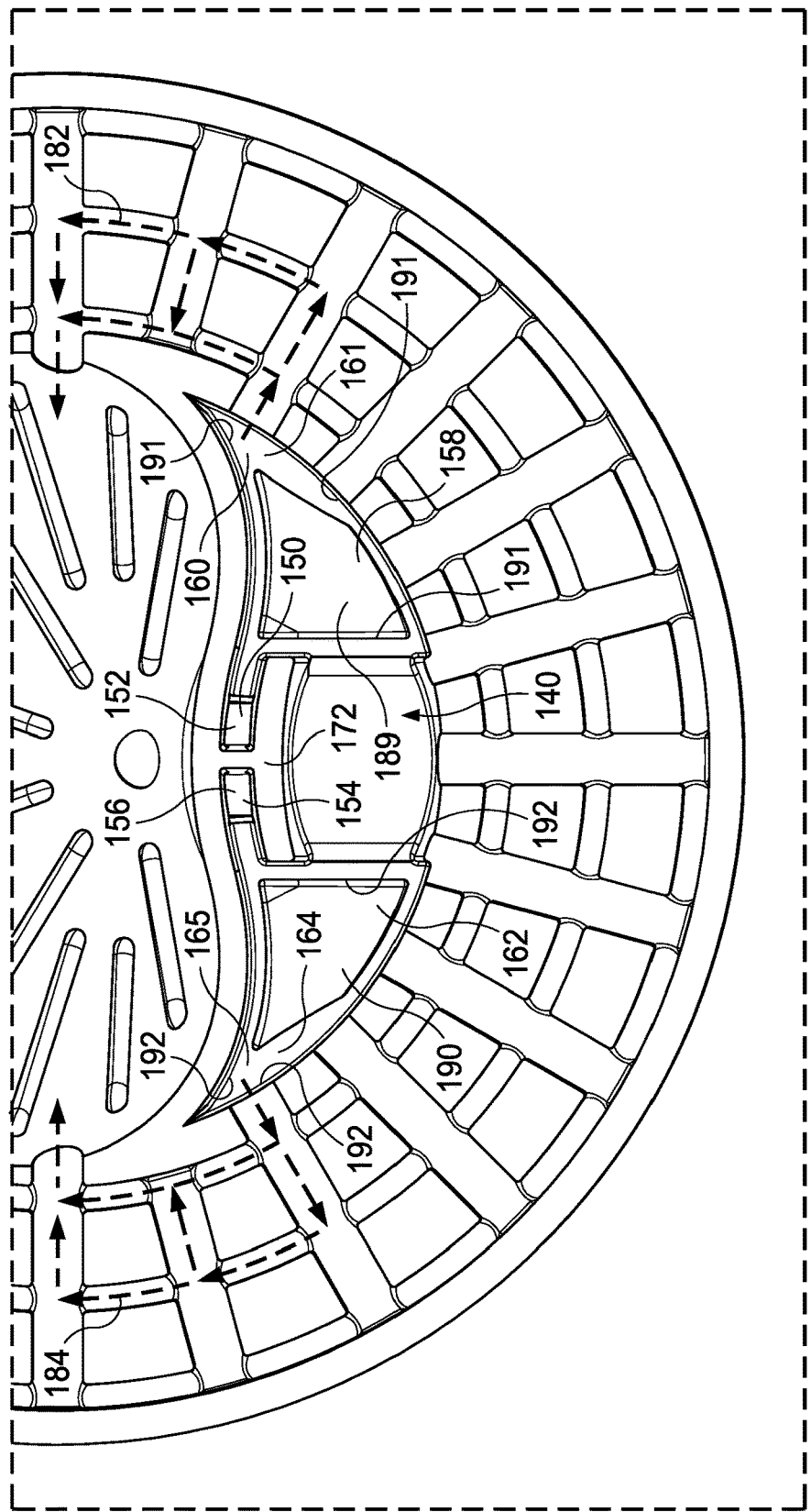

SYSTEM AND METHOD FOR INTERFACING WITH A REDUCED PRESSURE DRESSING

CROSS-REFERENCE TO RELATED APPLICATIONS

This application is a continuation of U.S. patent application Ser. No. 13/183,929, filed Jul. 15, 2011, entitled "System And Method For Interfacing With A Reduced Pressure Dressing", which claims the benefit of U.S. Provisional Application No. 61/365,252, filed Jul. 16, 2010, each of which is incorporated herein by reference.

BACKGROUND

1. Field of the Invention

The present invention relates generally to medical treatment systems, and more particularly, to reduced-pressure treatment systems, apparatuses, and methods for applying reduced pressure to a tissue site.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifolding device. The porous pad contains cells or pores that are capable of distributing reduced pressure to the tissue and channeling fluids that are drawn from the tissue. The porous pad often is incorporated into a dressing having other components that facilitate treatment.

SUMMARY

The problems presented by existing reduced-pressure systems are solved by the systems, apparatuses, and methods of the illustrative embodiments described herein. In one embodiment, a reduced-pressure interface for connecting a reduced-pressure source to a manifold pad to treat a tissue site on a patient with reduced pressure is provided and includes a conduit housing having a cavity divided by a dividing wall into a reduced-pressure-application region and a pressure-detection region. The reduced-pressure interface further includes a reduced-pressure port disposed within the reduced-pressure-application region, a pressure-detection port disposed within the pressure-detection region, and a base connected to the conduit housing, the base having a manifold-contacting surface. The dividing wall includes a surface substantially coplanar with the manifold-contacting surface.

In another illustrative embodiment, a reduced-pressure interface for connecting a reduced-pressure source to a manifold pad to treat a tissue site on a patient with reduced pressure includes a conduit housing having a first cavity and a second cavity, the first cavity separated from the second cavity by a wall. The reduced-pressure interface further includes a reduced-pressure port within the first cavity, a pressure-detection port within the second cavity, a flange connected to the conduit housing, the flange having a manifold-contacting surface, and at least one channel disposed in the manifold-contacting surface of the flange to transmit reduced pressure from the first cavity to the second cavity.

In another illustrative embodiment, a reduced-pressure interface for connecting a reduced-pressure source to a manifold pad to treat a tissue site on a patient with reduced pressure includes a conduit housing having a cavity divided by a dividing wall into a reduced-pressure-application region and a pressure-detection region. The reduced-pressure source further includes a pressure-detection lumen disposed within the pressure-detection region, at least one fluid trap within the pressure-detection region proximate the pressure-detection lumen, and a base connected to the conduit housing, the base having a manifold-contacting surface.

In another illustrative embodiment, a method of providing reduced-pressure treatment to a tissue site of a patient includes positioning a reduced-pressure interface proximate a manifold pad positioned at the tissue site. A portion of the manifold pad is drawn into a first cavity of the reduced-pressure interface by delivering a reduced pressure to the first cavity, and a fluid flows between a cavity surface of the first cavity and the manifold pad.

In another illustrative embodiment, a reduced-pressure treatment system for treating a tissue site on a patient includes a manifold pad for placing proximate the tissue site and a reduced-pressure interface fluidly coupled to the manifold pad. The reduced-pressure interface includes a conduit housing having a cavity divided by a dividing wall into a reduced-pressure-application region and a pressure-detection region. The reduced-pressure interface further includes a reduced-pressure port disposed within the reduced-pressure-application region, a pressure-detection port disposed within the pressure-detection region, a base connected to the conduit housing, the base having a manifold-contacting surface, and wherein the dividing wall includes a surface substantially coplanar with the manifold-contacting surface. The reduced-pressure treatment system further includes a reduced-pressure source fluidly coupled to the reduced-pressure interface and operable to supply reduced pressure to the manifold pad.

In another illustrative embodiment, a reduced-pressure treatment system for treating a tissue site on a patient includes a manifold pad for placing proximate the tissue site and a reduced-pressure interface fluidly coupled to the manifold pad. The reduced-pressure interface includes a conduit housing having a first cavity and a second cavity, and a wall for separating the first cavity from the second cavity. The reduced-pressure interface further includes a reduced-pressure port within the first cavity, a pressure-detection port within the second cavity, a flange connected to the conduit housing, the flange having a manifold-contacting surface, and at least one channel disposed in the manifold-contacting surface of the flange to transmit reduced pressure from the first cavity to the second cavity. The reduced-pressure treatment system further includes a reduced-pressure source fluidly coupled to the reduced-pressure interface and operable to supply reduced pressure to the manifold pad.

In another illustrative embodiment, a reduced-pressure treatment system for treating a tissue site on a patient includes a manifold pad for placing proximate the tissue site and a reduced-pressure interface fluidly coupled to the manifold pad. The reduced-pressure interface includes a conduit housing having a cavity divided by a dividing wall into a reduced-pressure-application region and a pressure-detection region. The reduced-pressure interface further includes a pressure-detection lumen disposed within the pressure-detection region, at least one fluid trap within the pressure-detection region proximate the pressure-detection lumen, and a base connected to the conduit housing having a manifold-contacting surface. The reduced pressure treatment system further includes a reduced-pressure source fluidly coupled to the reduced-pressure interface and operable to supply reduced pressure to the manifold pad.

Other objects, features, and advantages of the illustrative embodiments will become apparent with reference to the drawings and detailed description that follow.

BRIEF DESCRIPTION OF THE DRAWINGS

FIG. 5 illustrates a bottom view of the reduced-pressure interface of FIG. 2;

FIG. 5A illustrates a detailed view of a portion or the reduced-pressure interface of FIG. 5;

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims. Unless otherwise indicated, as used herein, "or" does not require mutual exclusivity.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

Figure 1:
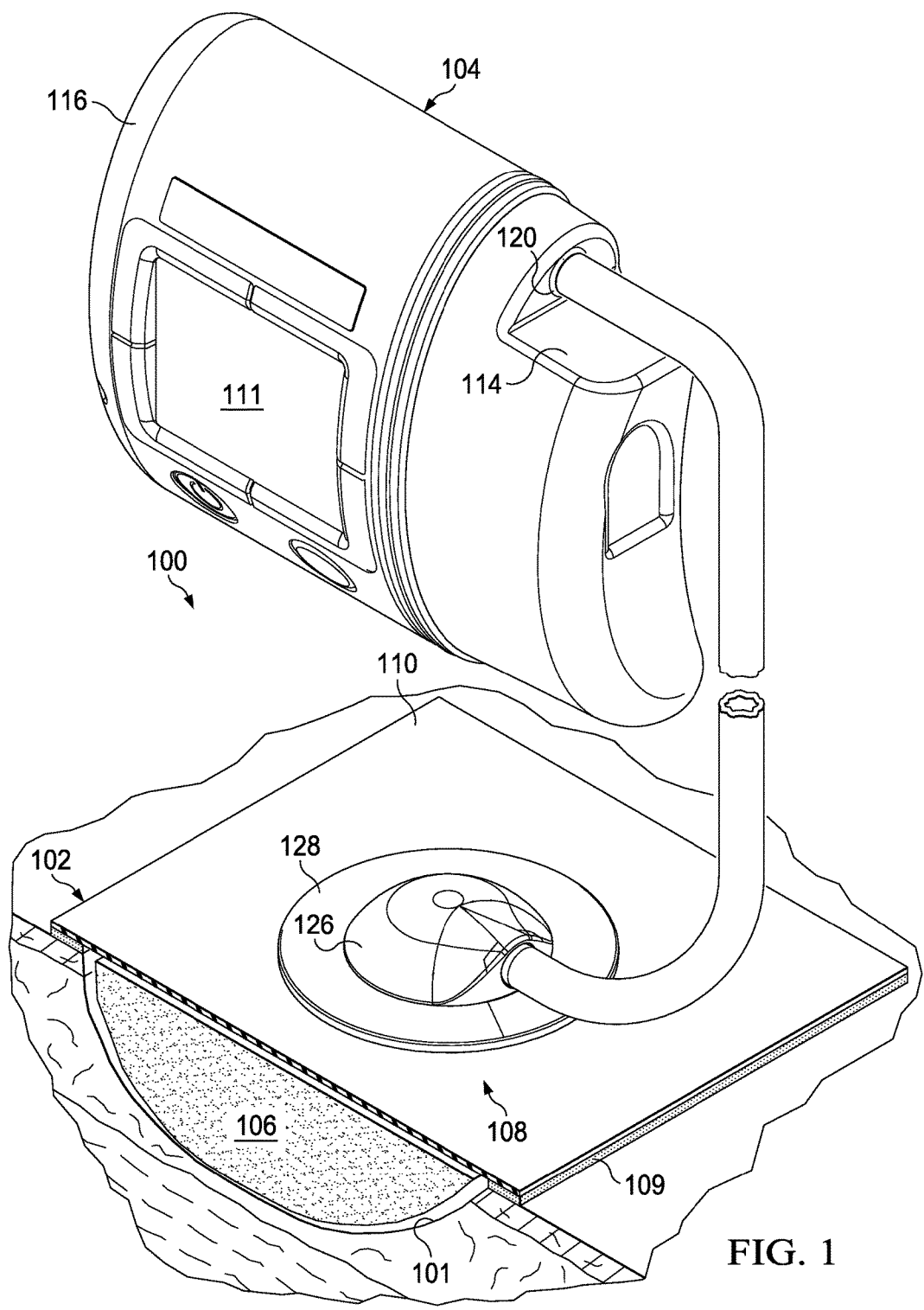
FIG. 1 illustrates a schematic diagram, in perspective view with a portion in cross-section, of a reduced-pressure treatment system for applying reduced pressure to a tissue site, according to an illustrative embodiment.
Figure 2:
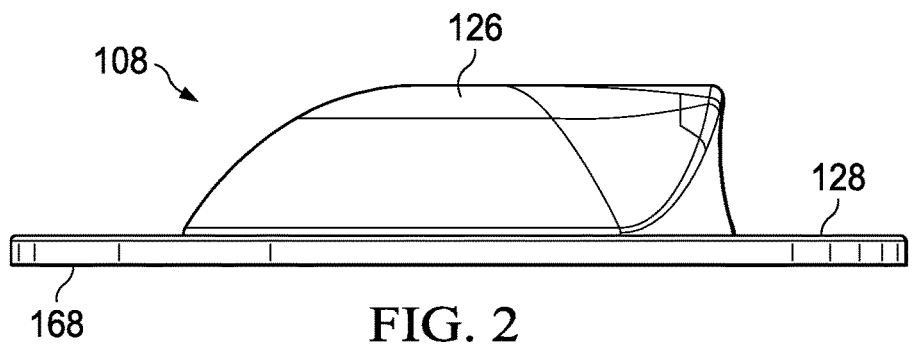
FIG. 2 illustrates a side view of a reduced-pressure interface of the reduced-pressure treatment system of FIG. 1.
Figure 3:
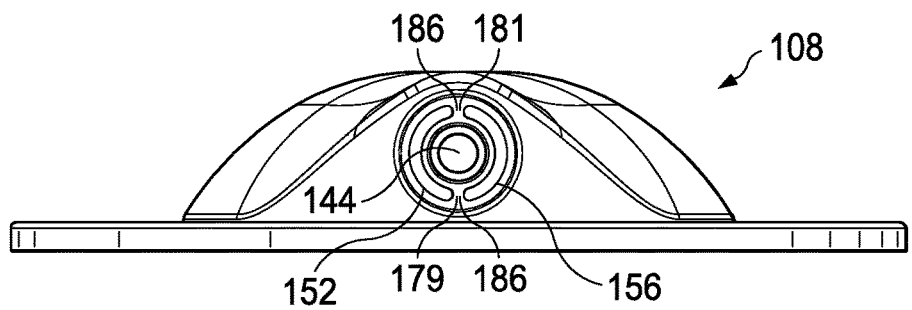
FIG. 3 illustrates a front view of the reduced-pressure interface of FIG. 2.
Figure 4:
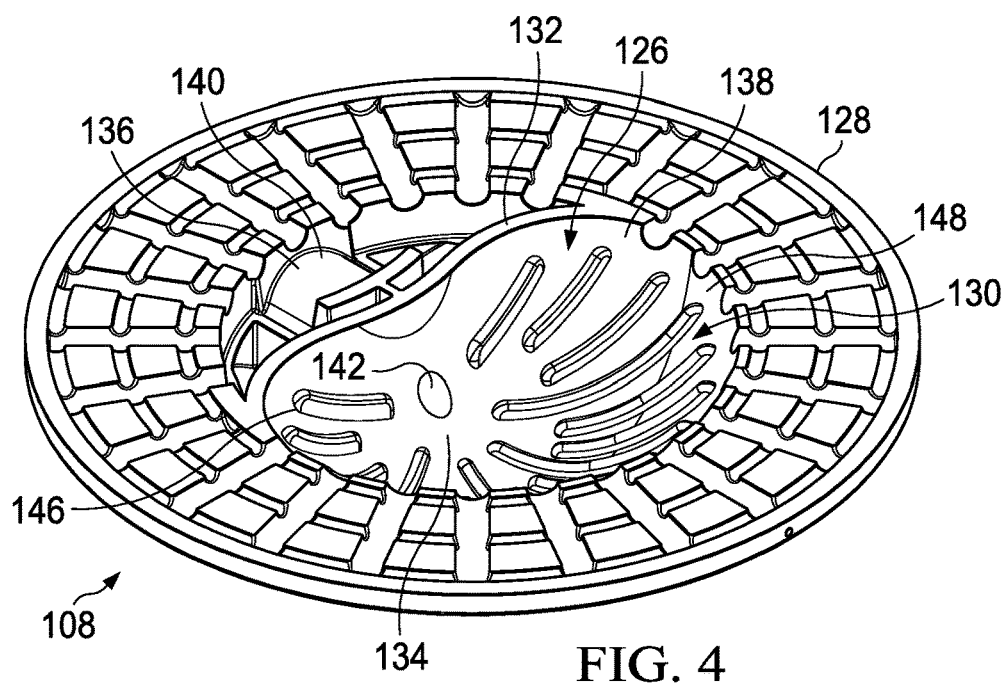
FIG. 4 illustrates a bottom, perspective view of the reduced-pressure interface of FIG. 2.
Figure 6:
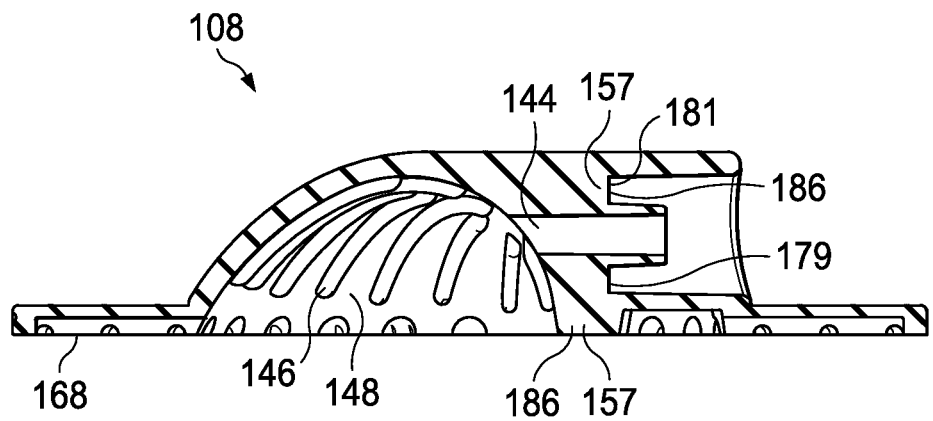
FIG. 6 illustrates a cross-sectional, side view of the reduced-pressure interface of FIG. 5 taken at line 6-6.
Figure 7:
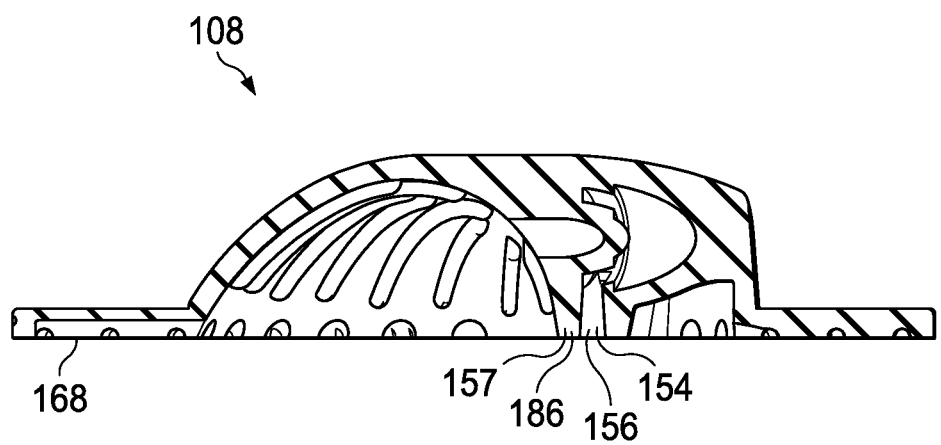
FIG. 7 illustrates a cross-sectional, side view of the reduced-pressure interface of FIG. 5 taken at line 7-7.

Referring to FIG. 1, an illustrative embodiment of a reduced-pressure treatment system 100 for treating a tissue site 101 on a patient with reduced pressure includes a dressing 102 placed proximate to the tissue site 101, and a reduced-pressure treatment device 104 fluidly coupled to the dressing 102. As used herein, the term "tissue site" may refer to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The dressing 102 may include a manifold pad 106 place proximate the tissue site 101, a reduced-pressure interface 108 fluidly coupled to the manifold pad 106, and a sealing member 110. The sealing member 110, or drape, may be placed over the manifold pad 106 and a portion of a patient's epidermis 103 to create a fluid seal between the sealing member 110 and the epidermis 103. The sealing member 110 may include an adhesive 109 or bonding agent to secure the sealing member 110 to the epidermis 103. In one embodiment, the adhesive 109 may be used to create a seal between the sealing member 110 and the epidermis 103 to prevent leakage of reduced pressure from the tissue site 101. In another embodiment, a seal layer (not shown) such as, for example, a hydrogel or other material may be disposed between the sealing member 110 and the epidermis 103 to augment or substitute for the sealing properties of the adhesive 109. As used herein, "fluid seal" means a seal adequate to maintain reduced pressure at a desired site given the particular reduced-pressure source involved.

The term "manifold" as used herein generally refers to a substance or structure that is provided to assist in applying reduced pressure to, delivering fluids to, or removing fluids from the tissue site 101. The manifold pad 106 typically includes a plurality of flow channels or pathways that distribute fluids provided to and removed from the tissue site around the manifold pad 106. In one illustrative embodiment, the flow channels or pathways are interconnected to improve distribution of fluids provided or removed from the tissue site 101. Examples of manifold pads 106 may include, for example, without limitation, devices that have structural elements arranged to form flow channels, such as, for example, cellular foam, open-cell foam, porous tissue collections, liquids, gels, and foams that include, or cure to include, flow channels. In one embodiment, the manifold pad 106 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. Other embodiments may include closed cells.

The reduced-pressure interface 108 may be positioned adjacent to or coupled to the sealing member 110 to provide fluid access to the manifold pad 106. In one embodiment, the sealing member 110 is placed over the reduced-pressure interface 108 and a portion of the patient's epidermis 103 to create a fluid seal between the sealing member 110 and the epidermis 103. The sealing member 110 has an aperture (not shown) for providing fluid access between the reduced-pressure interface 108 and the manifold pad 106. The sealing member 110 is placed adjacent to the manifold pad 106 to create a fluid seal between the sealing member 110 and the epidermis 103. The reduced-pressure interface 108 is placed on top of and fluidly sealed to the sealing member 110. A reduced-pressure delivery conduit 112 fluidly couples the reduced-pressure treatment device 104 and the reduced-pressure interface 108. The reduced-pressure interface 108 allows the reduced pressure to be delivered to the tissue site 101. While the amount and nature of reduced pressure applied to the tissue site 101 will typically vary according to the application, the reduced-pressure treatment device 104 will typically provide reduced pressure between −5 mm Hg and −500 mm Hg and more typically between −100 mm Hg and −300 mm Hg.

The reduced-pressure treatment device 104 may include a collection canister 114 in fluid communication with a reduced-pressure source 116. The reduced-pressure delivery conduit 112 may be a multi-lumen tube that provides a continuous conduit between the reduced-pressure interface 108 and an inlet 120 positioned on the collection canister 114. Liquids or exudates communicated from the manifold pad 106 through the reduced-pressure delivery conduit 112 are removed from the reduced-pressure delivery conduit 112 and retained within the collection canister 114.

In the embodiment illustrated in FIG. 1, the reduced-pressure source 116 is an electrically-driven vacuum pump. In another implementation, the reduced-pressure source 116 may instead be a manually-actuated or manually-charged pump that does not require electrical power. The reduced-pressure source 116 instead may be any other type of reduced pressure pump, or alternatively a wall suction port such as those available in hospitals and other medical facilities. The reduced-pressure source 116 may be housed within or used in conjunction with the reduced-pressure treatment device 104, which may also contain sensors, processing units, alarm indicators, memory, databases, software, display units, and user interfaces 111 that further facilitate the application of reduced pressure treatment to the tissue site 101. In one example, pressure-detection sensors (not shown) may be disposed at or near the reduced-pressure source 116. The pressure-detection sensors may be fluidly connected to one or more lumens in the reduced-pressure delivery conduit 112 such that a pressure reading identical to or approximating the pressure at the tissue site may be ascertained. The pressure-detection sensors may communicate with a processing unit that monitors and controls the reduced pressure that is delivered by the reduced-pressure source 116.

Referring now to FIGS. 2-8A, an illustrative embodiment of the reduced-pressure interface 108 is presented in more detail. The reduced-pressure interface 108 includes a conduit housing 126 and a base 128. The conduit housing 126 includes a cavity 130 that may be "dome" shaped. The cavity 130 may be divided by a wall or dividing wall 132 into a first cavity 134 and a second cavity 136. The first cavity 134 is a reduced-pressure-application region 138 and the second cavity 136 is a pressure-detection region 140.

The reduced-pressure-application region 138 includes a reduced-pressure port 142 connected to a reduced-pressure lumen 144. The reduced-pressure port 142 and the reduced-pressure lumen 144 are operable to deliver reduced pressure to, and remove fluids from, the manifold pad 106 (see FIG. 1). The reduced-pressure-application region 138 may further include ridges 146. In an alternative embodiment, (not shown) the ridges 146 may be combined with, or substituted for, channels. Since the manifold pad 106 may be drawn into the first cavity 134 when reduced pressure is applied, the ridges 146 (or channels) may help prevent the manifold pad 106 from creating a seal against a cavity surface 148 of the reduced-pressure-application region 138.

Referring primarily to FIG. 5A, but also with reference to FIGS. 2-8A, the pressure-detection region 140 includes a first pressure-detection port 150 connected to a first pressure-detection lumen 152 and in one embodiment may further include a second pressure-detection port 154 connected to a second pressure-detection lumen 156. The pressure-detection ports 150, 154 and the respective pressure-detection lumens 152, 156 may permit fluid communication with the pressure-detection sensors located in the reduced-pressure treatment device 104 (see FIG. 1) such that the pressure or pressure fluctuations at the tissue site may be ascertained. As previously noted, information regarding pressure data and fluctuations may be communicated via reduced-pressure delivery conduit 112 (see FIG. 1). In the embodiments in which two pressure detection ports 150, 154 are provided, the first pressure-detection port 150 and the first pressure-detection lumen 152 are physically separate from the second pressure-detection port 154 and second pressure-detection lumen 156 to help reduce the possibility of both pressure-detection lumens 152, 156 being blocked by exudates or other means of blockage.

Referring again to FIGS. 2-8A, the first pressure-detection port and lumen 150 and 152 may be physically separated from the second pressure-detection port and lumen 154 and 156 by a barrier 157. The barrier 157 includes a surface 172 that may be substantially coplanar with a surface 170 of the dividing wall 132. The barrier 157 may include a first portion 186 substantially perpendicular to a second portion 188. The first portion 186 is substantially perpendicular to and connected to the dividing wall 132 and separates the first pressure-detection port and lumen 150 and 152 from the second pressure-detection port and lumen 154 and 156. The first portion 186 may be attached to the reduced-pressure lumen 144 at a first position 179 and a second position 181, wherein the first position 179 is opposed to the second position 181, to maintain separation between the pressure-detection lumens 152, 156. The second portion 188 of the barrier 157 may be substantially parallel to the dividing wall 132. The second portion 188 may function to shield the pressure-detection ports 150, 154 from fluids entering the pressure-detection region 140.

Figures 8, 8A:
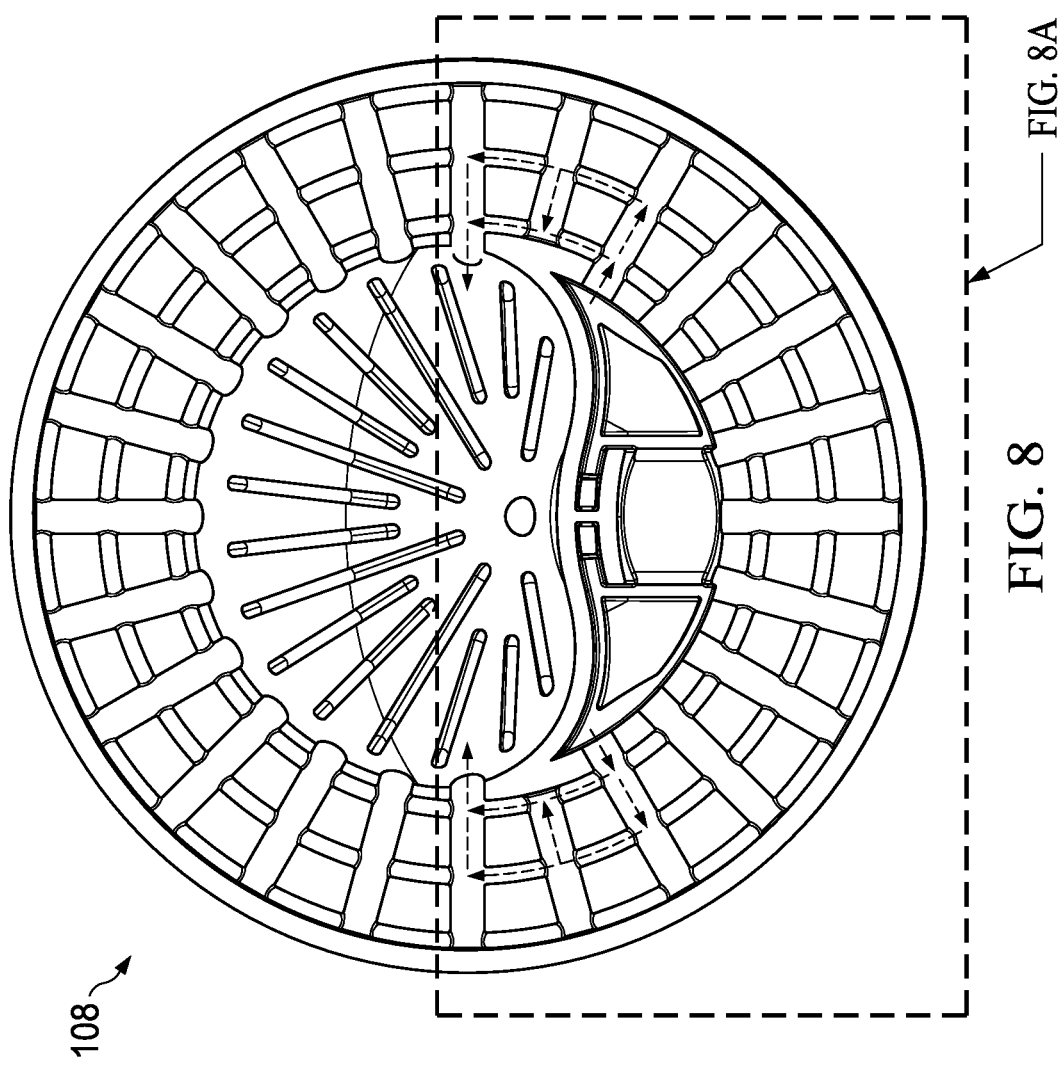
FIG. 8 illustrates a bottom view of the reduced-pressure interface of FIG. 2.
FIG. 8A illustrates a detailed view of a portion of the reduced-pressure interface of FIG. 8.

Referring now primarily to FIG. 8A, the pressure-detection region 140 may further include a first fluid trap 158 proximate the first pressure-detection port 150 for trapping or discouraging liquids from entering the first pressure-detection port 150. The first fluid trap 158 may include a first flow concentration region 160 for diverting fluids trapped in the first fluid trap 158 out of the pressure-detection region 140. Likewise, the pressure-detection region 140 may include a second fluid trap 162 proximate the second pressure-detection port 154 for trapping liquids from entering the second pressure-detection port 154. The second fluid trap 162 may include a second flow concentration region 164 for diverting fluids trapped in the second fluid trap 162 out of the pressure-detection region 140. The first fluid trap 158 and the second fluid trap 162 may be partially recessed within the pressure-detection region 140. The first fluid trap 158 may form a first basin 189 at least partially surrounded by first basin walls 191, and the second fluid trap 162 may form a second basin 190 at least partially surrounded by second basin walls 192.

The first flow concentration region 160 may have a first apex 161 formed at the divergence of at least two of the first basin walls 191 to create an acute angle, and the second flow concentration region 164 may have a second apex 165 formed at the divergence of at least two of the second basin walls 192 to create an acute angle. The first apex 161 may be diametrically opposed to the second apex 165. The flow concentration regions 160, 164 concentrate the flow of fluids into their respective apexes 161, 165. The first apex 161 may help divert fluids from the pressure-detection region 140 into the base 128 along a flow path 182. Likewise, the second apex 165 may help divert fluids from the pressure-detection region 140 into the base 128 along a flow path 184.

Referring again to FIGS. 2-8A, the base 128 of the reduced-pressure interface 108 may be a flange 166. The base 128 is connected to the conduit housing 126 and has a manifold-contacting surface 168. The manifold-contacting surface 168 may be substantially coplanar with the surfaces 170 of dividing wall 132 and the surfaces 172 of barrier 157.

The base 128 may include one or more channels 174 disposed in the manifold-contacting surface 168 for transmitting reduced pressure and fluids between the reduced-pressure-application region 138 and pressure-detection region 140. For example, the base 128 may include at least one continuous, circumferential channel 175. If more than one circumferential channels 175 are provided, the channels may be concentrically arranged. The base 128 may further include at least one first radial channel 176 or at least one second radial channel 178 disposed in the manifold-contacting surface 168. The first radial channel 176 may be in fluid communication with the reduced-pressure-application region 138 and the second radial channel 178 may be in fluid communication with the pressure-detection region 140. The circumferential channel 175 provides fluid communication between the first radial channel 176 and the second radial channel 178 for communicating reduced-pressure and fluids between the reduced-pressure-application region 138 and the pressure-detection region 140.

In operation, the channels 174 may transmit reduced pressure from the reduced-pressure-application region 138 to the pressure-detection region 140. Likewise, the channels 174 may help divert fluids from the apexes 161, 165 along respective flow paths 182, 184 into the reduced-pressure-application region 138.

In one embodiment, a method for providing reduced pressure treatment to a tissue site 101 includes positioning the reduced-pressure interface 108 proximate the manifold pad 106 positioned at the tissue site 101. The method may also include drawing a portion of the manifold pad 106 into the first cavity 134 of the reduced-pressure interface 108 by delivering the reduced pressure to the first cavity 134. The portion of the manifold pad 106 drawn into the first cavity 134 may substantially or completely fill the first cavity 134 such that the portion of the manifold pad 106 is in physical contact with the cavity surface 148 or the reduced-pressure port 142. In this embodiment, fluid may flow between the cavity surface 148 and the manifold pad 106. Fluid may be directed between the ridges 146 positioned on the cavity surface 148. Additionally, pressure within the second cavity 136 may be monitored.

In operation, drawing the portion of the manifold pad 106 into the first cavity 134 may allow the portion of the manifold pad 106 to decompress creating a pressure gradient within the manifold pad 106. The pressure gradient created within the manifold pad 106 may help encourage fluids towards the reduced-pressure port 142.

The reduced-pressure interface 108 may be constructed from materials known in the art that provide the appropriate flexibility and comfort to the patient while maintaining sufficient rigidity or resilience to maintain fluid communication pathways, such as ports, lumens, and channels.

It should be apparent from the foregoing that an invention having significant advantages has been provided. While the invention is shown in only a few of its forms, it is not just limited but is susceptible to various changes and modifications without departing from the spirit thereof.

We claim:

1. A reduced-pressure interface for connecting a reduced-pressure source to a manifold pad to treat a tissue site on a patient with reduced pressure, the reduced-pressure interface comprising:
    a conduit housing having a first cavity and a second cavity;
    a reduced-pressure port within the first cavity;
    a pressure-detection port within the second cavity;
    a flange connected to the conduit housing, the flange having a manifold-contacting surface;
    a wall fluidly separating the first cavity and the second cavity and having a surface substantially coplanar with the manifold-contacting surface of the flange,
    wherein the reduced-pressure port is located within a surface of the wall facing the first cavity and fluidly separating the first cavity and the second cavity; and
    at least one channel disposed in the manifold-contacting surface of the flange to transmit reduced pressure from the first cavity to the second cavity.

2. The reduced-pressure interface of claim 1, further comprising:
    a flow-concentration region within the second cavity to concentrate a flow of fluids from the second cavity into the at least one channel in the manifold-contacting surface.

3. The reduced-pressure interface of claim 1, wherein the at least one channel further comprises:
    a first radial channel disposed in the manifold-contacting surface of the flange, the first radial channel in communication with the first cavity;
    a second radial channel disposed in the manifold-contacting surface of the flange, the second radial channel in communication with the second cavity; and
    wherein the at least one channel provides communication between the first radial channel and the second radial channel.

4. The reduced-pressure interface of claim 1, the reduced-pressure interface further comprising:
    a plurality of channels concentrically disposed in the manifold-contacting surface;
    a plurality of first radial channels disposed in the manifold-contacting surface, the plurality of first radial channels in communication with the first cavity;
    a plurality of second radial channels disposed in the manifold-contacting surface, the plurality of second radial channels in communication with the second cavity; and
    wherein the plurality of channels provides communication between the plurality of first radial channels and the plurality of second radial channels.

5. The reduced-pressure interface of claim 1, wherein the pressure-detection port is a first pressure-detection port, the reduced-pressure interface further comprising:
   a second pressure-detection port disposed within the second cavity;
   a first fluid trap having a first flow-concentration region, the first fluid trap interposed between the first pressure-detection port and a first fluid pathway;
   a second fluid trap having a second flow-concentration region, the second fluid trap interposed between the second pressure-detection port and a second fluid pathway; and
   wherein the first and second fluid traps are operable to divert fluid flow from the first and second pressure-detection ports.

6. The reduced-pressure interface of claim 5, the reduced-pressure interface further comprising:
   a barrier disposed between the first pressure-detection port and the second pressure-detection port operable to physically separate the first pressure-detection port from the second pressure-detection port; and
   wherein the barrier includes a barrier surface substantially coplanar with the manifold-contacting surface.

7. The reduced-pressure interface of claim 1, wherein the second cavity further comprises at least one fluid trap proximate the pressure-detection port.

8. The reduced-pressure interface of claim 1, wherein the pressure-detection port is a first pressure-detection port, the reduced-pressure interface further comprising:
   a second pressure-detection port disposed within the second cavity;
   a barrier disposed within the second cavity between the first pressure-detection port and the second pressure-detection port operable to physically separate the first pressure-detection port from the second pressure-detection port.

9. The reduced-pressure interface of claim 8, wherein the barrier includes a first portion that is substantially perpendicular to a second portion.

10. The reduced-pressure interface of claim 8, wherein the barrier includes a surface that is substantially coplanar with a surface of the wall fluidly separating the first cavity and the second cavity.

11. The reduced-pressure interface of claim 9, wherein the first portion is substantially perpendicular to and connected to the wall fluidly separating the first cavity and the second cavity.

12. The reduced-pressure interface of claim 9, wherein the second portion is substantially parallel to the wall fluidly separating the first cavity and the second cavity.

13. A method of providing reduced-pressure treatment to a tissue site of a patient, the method comprising:
   positioning a reduced-pressure interface proximate a manifold pad positioned at the tissue site, the reduced-pressure interface comprising:
      a conduit housing having a first cavity and a second cavity,
      a flange connected to the conduit housing, the flange having a manifold-contacting surface,
      a wall fluidly separating the first cavity and the second cavity and having a surface substantially coplanar with the manifold-contacting surface of the flange,
      a reduced-pressure port within the first cavity, wherein the reduced-pressure port is located within a surface of the wall facing the first cavity and fluidly separating the first cavity and the second cavity, and
      at least one channel disposed in the manifold-contacting surface of the flange to transmit reduced pressure from the first cavity to the second cavity;
   drawing a portion of the manifold pad into the first cavity of the reduced-pressure interface by delivering a reduced pressure to the first cavity; and
   flowing a fluid between a cavity surface of the first cavity and the manifold pad towards the reduced-pressure port.

14. The method of claim 13, the method further comprising:
   monitoring a pressure within the second cavity of the reduced-pressure interface.

15. The method of claim 13, wherein flowing the fluid further comprises:
   directing the fluid between ridges positioned on the cavity surface.

16. A reduced-pressure system for treating a tissue site, the reduced-pressure system comprising:
   a manifold pad for placing proximate the tissue site;
   a reduced-pressure interface fluidly coupled to the manifold pad, the reduced-pressure interface comprising:
      a conduit housing having a first cavity and a second cavity, the first cavity providing a reduced-pressure-application region and the second cavity providing a pressure-detection region,
      a reduced-pressure port disposed within the reduced-pressure-application region,
      a pressure-detection port disposed within the pressure-detection region,
      a base connected to the conduit housing, the base having a manifold-contacting surface,
      a dividing wall fluidly separating the first cavity and the second cavity and having a surface substantially coplanar with the manifold-contacting surface of the base, wherein the reduced-pressure port is located within a surface of the dividing wall facing the first cavity and fluidly separating the first cavity and the second cavity, and
      wherein the manifold-contacting surface provides at least one route of fluid communication between the first cavity and the second cavity; and
   a reduced-pressure source fluidly coupled to the reduced-pressure interface and operable to supply reduced pressure to the manifold pad.

17. The system of claim 16, wherein the at least one route of fluid communication between the first cavity and the second cavity comprises at least one channel disposed in the manifold-contacting surface to transmit reduced pressure from the reduced-pressure-application region to the pressure-detection region.

18. The system of claim 16, wherein the at least one route of fluid communication between the first cavity and the second cavity comprises:
   at least one circumferential channel disposed in the manifold-contacting surface to transmit reduced pressure from the reduced-pressure-application region to the pressure-detection region;
   a first radial channel disposed in the manifold-contacting surface, the first radial channel in communication with the reduced-pressure-application region;
   a second radial channel disposed in the manifold-contacting surface, the second radial channel in communication with the pressure-detection region; and
   wherein the at least one circumferential channel provides communication between the first radial channel and the second radial channel.

19. The system of claim 16, wherein the at least one route of fluid communication between the first cavity and the second cavity comprises:
a plurality of circumferential channels concentrically disposed in the manifold-contacting surface to transmit reduced pressure from the reduced-pressure-application region to the pressure-detection region;
a plurality of first radial channels disposed in the manifold-contacting surface, the plurality of first radial channels in communication with the reduced-pressure-application region;
a plurality of second radial channels disposed in the manifold-contacting surface, the plurality of second radial channels in communication with the pressure-detection region; and
wherein the plurality of circumferential channels provides communication between the plurality of first radial channels and the plurality of second radial channels.

20. The system of claim 16, wherein the at least one route of fluid communication between the first cavity and the second cavity comprises:
at least one channel disposed in the manifold-contacting surface providing communication between the pressure-detection region and the reduced-pressure-application region, wherein the manifold-contacting surface surrounds the pressure-detection region and the reduced-pressure-application region; and
a flow-concentration region within the pressure-detection region to concentrate a flow of fluids from the pressure-detection region into the at least one channel in the manifold-contacting surface.

21. The system of claim 16, the reduced-pressure interface further comprising:
at least one fluid trap within the pressure-detection region proximate the pressure-detection port.

22. The system of claim 16, wherein the pressure-detection port is a first pressure-detection port, the reduced-pressure interface further comprising:
a second pressure-detection port disposed within the pressure-detection region;
a first fluid trap having a first flow-concentration region, the first fluid trap interposed between the first pressure-detection port and a first fluid pathway;
a second fluid trap having a second flow-concentration region, the second fluid trap interposed between the second pressure-detection port and a second fluid pathway; and
wherein the first and second fluid traps are operable to divert fluid flow from the first and second pressure-detection ports.

23. The system of claim 22, the reduced-pressure interface further comprising:
a barrier disposed between the first pressure-detection port and the second pressure-detection port operable to physically separate the first pressure-detection port from the second pressure-detection port; and
wherein the barrier includes a barrier surface substantially coplanar with the manifold-contacting surface.

24. A reduced-pressure treatment system for treating a tissue site on a patient, the reduced-pressure treatment system comprising:
a manifold pad for placing proximate the tissue site;
a reduced-pressure interface fluidly coupled to the manifold pad, the reduced-pressure interface comprising:
a conduit housing having a first cavity and a second cavity,
a reduced-pressure port within the first cavity,
a pressure-detection port within the second cavity,
a flange connected to the conduit housing, the flange having a manifold-contacting surface,
a wall fluidly separating the first cavity and the second cavity and having a surface substantially coplanar with the manifold-contacting surface of the flange,
wherein the reduced-pressure port is located within a surface of the wall facing the first cavity and fluidly separating the first cavity and the second cavity, and
at least one channel disposed in the manifold-contacting surface of the flange to transmit reduced pressure from the first cavity to the second cavity; and
a reduced-pressure source fluidly coupled to the reduced-pressure interface and operable to supply reduced pressure to the manifold pad.

25. A reduced-pressure system for treating a tissue site, the reduced-pressure system comprising:
a manifold pad for placing proximate the tissue site;
a reduced-pressure interface fluidly coupled to the manifold pad, the reduced-pressure interface comprising:
a conduit housing having a first cavity and a second cavity, the first cavity providing a reduced-pressure-application region and the second cavity providing a pressure-detection region,
a reduced-pressure port within the first cavity,
a pressure-detection lumen disposed within the pressure-detection region,
at least one fluid trap within the pressure-detection region proximate the pressure-detection lumen,
a base connected to the conduit housing, the base having a manifold-contacting surface
a dividing wall fluidly separating the first cavity and the second cavity and having a surface substantially coplanar with the manifold-contacting surface of the base,
wherein the reduced-pressure port is located within a surface of the dividing wall facing the first cavity and fluidly separating the first cavity and the second cavity, and
wherein the manifold-contacting surface provides at least one route of fluid communication between the first cavity and the second cavity; and
a reduced-pressure source fluidly coupled to the reduced-pressure interface and operable to supply reduced pressure to the manifold pad.

* * * * *